(12) United States Patent
Hatanaka et al.

(10) Patent No.: US 8,043,666 B2
(45) Date of Patent: Oct. 25, 2011

(54) PHOTOREACTIVE COMPOUND, PHOTOREACTIVE POLYAMINE AND METHOD FOR PRODUCING POLYAMINE SHEET

(75) Inventors: Yasumaru Hatanaka, Toyama (JP); Takenori Tomohiro, Toyoma (JP); Gabin Vic, Paris (FR)

(73) Assignee: University of Toyama, Toyama-shi (JP)

( * ) Notice: Subject to any disclaimer, the term of this patent is extended or adjusted under 35 U.S.C. 154(b) by 1047 days.

(21) Appl. No.: 11/573,824

(22) PCT Filed: Aug. 17, 2005

(86) PCT No.: PCT/JP2005/015013
§ 371 (c)(1),
(2), (4) Date: Oct. 12, 2007

(87) PCT Pub. No.: WO2006/019116
PCT Pub. Date: Feb. 23, 2006

(65) Prior Publication Data
US 2008/0069969 A1    Mar. 20, 2008

(30) Foreign Application Priority Data

Aug. 17, 2004   (JP) ................. 2004-237605

(51) Int. Cl.
C08G 73/06 (2006.01)
B05D 3/06 (2006.01)
C07D 229/02 (2006.01)
(52) U.S. Cl. .............. 427/520; 528/423; 548/960
(58) Field of Classification Search .............. None
See application file for complete search history.

(56) References Cited

U.S. PATENT DOCUMENTS
2003/0099930 A1   5/2003  Graves et al.
2004/0043046 A1*  3/2004  Vic et al. ............ 424/401

FOREIGN PATENT DOCUMENTS
JP   2001 178472   7/2001
JP   2004 049230   2/2004
JP   2004 510147   4/2004
WO   01 06011      1/2001

OTHER PUBLICATIONS

Hatanaka, Yasumaru et al. " A Rapid and Efficient Method for Identifying Photoaffinity Biotynylated Sites within Protein", J. Am. Chem. Soc., vol. 120, No. 2, pp. 453-454, 1998.
Hatanaka, Yasumaru,"Organic Chemistry for Structural Biology:Probing the Functional Structure of Proteins by Photoaffinity Labeling", Journal of Synthetic Organic Chemistry, vol. 56, No. 7, pp. 581-590, 1998.
Ivanova, Elena P. et al.," Poly(L-lysine)-mediated Immobilisation of Oligonucleotides on Carboxy-rich Polymer Surfaces" Biosensors and Bioelectronics, vol. 19, No. 11, pp. 1363-1370, 2004.
A.N.J.A. Ridder, et al., "Photo-Crosslinking Analysis of Preferential Interactions between a Transmembrane Peptide and Matching Lipids", Biochemistry, vol. 43, Mar. 23, 2004, pp. 4482.4489.
Supplementary European Search Report mailed Nov. 26, 2010, in 05780373, filed Aug. 17, 2005.

* cited by examiner

*Primary Examiner* — Sun Jae Loewe
(74) *Attorney, Agent, or Firm* — Oblon, Spivak, McClelland, Maier & Neustadt, L.L.P.

(57) ABSTRACT

Disclosed is a polyamine sheet which is usable for DNA chips or protein chips. Also disclosed are a photoreactive polyamine used for producing such a polyamine sheet, and a photoreactive compound which can be a raw material for such a photoreactive polyamine. Specifically disclosed are a photoreactive compound having a diazirine group as a photoreactive group, a photoreactive polyamine compound produced from such a photoreactive compound and a polyamine, a polyamine sheet using such a photoreactive polyamine compound, and a method for producing such a polyamine sheet.

2 Claims, 3 Drawing Sheets

PHOTOREACTIVE COMPOUND, PHOTOREACTIVE POLYAMINE AND METHOD FOR PRODUCING POLYAMINE SHEET

TECHNICAL FIELD

The present invention relates to a photoreactive compound, a photoreactive polyamine and a method for producing a polyamine sheet. Specifically, the present invention relates to a photoreactive compound and a photoreactive polyamine having a diazirine group as a photoreactive group, and further relates to a method of producing a polyamine sheet using the aforementioned photoreactive polyamine.

BACKGROUND ART

DNA chip technology is a technology for identifying a target expressed gene, by labeling the gene, hybridizing to DNA on a glass surface or silicon substrate, and observing the positions of immobilization. DNA chips make use of the spotting technique whereby cDNA or synthesized oligonucleotides are immobilized on a substrate, or the in situ (on chip) technique wherein oligonucleotides are directly synthesized on a substrate. A representative example of the latter is the "Gene Chip" of Affymetrix. In the spotting technique, DNA fragments of from several hundred to up to ten thousand types of genes can be arrayed within an area of several square centimeters on a substrate such as a glass slide, then subjected to an immobilization method using primarily electrostatic bonding and covalent bonding (Non-patent Document 1).

In immobilization by electrostatic bonding, a glass slide coated with polycations is spotted with DNA and oligonucleotides which are polyanions. The immobilization efficiency depends on their length. In order to observe a difference of one base in SNP analysis, it is necessary to use synthesized oligonucleotides of 20-30 bases, but if the lengths are short, it is difficult to achieve stable immobilization of DNA, and the efficiency decreases. Additionally, polyamines have been used for modification of the substrate surface of DNA chips, but they are coated on the entire solid phase, making detection of trace amounts of genes difficult due to non-specific adsorption of DNA (Non-patent Documents 2 and 3).

On the other hand, in the immobilization method using covalent bonding, a substrate is treated with a silane coupling agent having amino groups, aldehyde groups, epoxy groups, activated ester groups, vinyl groups, and the like, then bound to DNA to the ends of which amino groups, aldehyde groups, thiol groups, biotin and the like have been introduced. By this method, the stability of immobilized molecules is increased, but in cases where hybridization and the like are carried out, it is easily affected by the substrate surface, and in particular, there are reports that the first 20-30 bases from the surface are hardly used, so that problems of specificity and reproducibility arise quite easily. Recently, hybridization to synthesized oligomers covalently bonded to the surface under a liquid phase environment has become possible by arraying minute pieces of polyacrylamide gel on the glass surface, but a prior surface treatment process such as attachment of functional groups on the glass surface is unavoidable (Non-patent Document 4).

The search for drug discovery candidates and their target molecules efficiently by proteomics must depend on a direct and rational analysis based upon the ligand recognition ability of proteins. However, the DNA chips and protein chips available until now have the aforementioned drawbacks, and therefore do not have adequate performance for such analysis.

Non-patent Document 1: *DNA Chip Ouyou Gijutsu* (2000), Tadashi Matsunaga (ed.), Published by CMC Publishing Co., Ltd.

Non-patent Document 2: "DNA chip technology and its applications", *Protein, Nucleic Acids and Enzyme* 43(13), (1998), Fusao Kimizuka, Ikunoshin Katoh, Published by Kyoritsu Shuppan CO., LTD, pp. 2004-2011.

Non-patent Document 3. Barrett J. C, Kawasaki E. S., "Microarrays: the use of oligonucleotides and cDNA for the analysis of gene expression", *Drug Discov Today*, 8, 134-141, 2003.

Non-patent Document 4: Yershov G, Barsky V, Belgovskiy A, Kirillov E, Kreindlin E, Ivanov I, Parinov S, Cuschin D, Drobishev A, Dubilev S, Mirzabekov A., "DNA analysis and diagnostics on oligonucleotide microchips", *Proc. Natl. Acad. Sci.* USA, 93, 4913-4918, 1996.

DISCLOSURE OF THE INVENTION

Problems to be Solved by the Invention

In making DNA chips and protein chips as described above, the following problems still remain to be solved.

(1) Conventionally, polyamines are used for modification of the DNA chip substrate surface, but detection of trace amounts of genes is difficult because of non-specific adsorption of DNA due to coating of the entire solid phase.

(2) Generally, glass slides used for DNA chips and protein chips require a surface treatment in accordance with the purpose.

(3) For bonding of biological molecules on solid phase surfaces, a liquid phase environment needs to be provided by a surface treatment.

The purpose of the present invention is to offer a material and method for directly bonding polyamines to the surface of resin substrates such as polypropylene using photolithography. More specifically, the purpose of the present invention is to provide polyamine sheets that are usable for DNA chips and protein chips, photoreactive polyamines used for the fabrication of polyamine sheets, and photoreactive compounds as raw materials such as photoreactive polyamines.

Means for Solving the Problems

The present inventors have been engaged in research in an advanced technology known as the photoaffinity method that uses photoreactions to irreversibly join specific ligands and proteins using photoreactions, and have developed a unique high-speed photoaffinity method utilizing diazirine derivatives as photoreactive groups (see the following Reference Documents 1-7).

Reference Document 1: "Multifunctional photoprobes for rapid protein identification", *In Chemical Genomics*, by Darvas F., Guttman A., and Dorman G. (Eds.) 199-214, Marcel Dekker Inc., New York, 2003.

Reference Document 2: "Labeling in Drug Discovery and Developments: Chemical Gateway for Entering Proteomic Frontier", *Curr. Top. Med. Chem.*, 2, 271-288, 2002.

Reference Document 3: "A novel approach for affinity-based screening of target specific ligands: Application of photoreactive D-glyceraldehyde-3-phosphate dehydrogenase", *Bioconjugate Chem.*, 14, 849-852 (2003).

Reference Document 4: "Improvement in the properties of 3-phenyl-3-trifluoromethyldiazirine based-photoreactive bis-glucose probes for GLUT4 following substitution on the phenyl ring", *Chem. Pharm. Bull.*, 50, 1004-1006, 2002.

Reference Document 5: "One-step Synthesis of Biotinyl Photoprobes from Unprotected Carbohydrates", *J. Org. Chem.*, 65, 5639-5643, 2000.

Reference Document 6: "A Rapid and Efficient Method for Identifying Photoaffinity Biotinylated Sites within Proteins", *J. Am. Chem. Soc.*, 120, 453-454, 1998

Reference Document 7: JP-A 2000-319262 (Title of the Invention, "Phenyldiazirine Compound and Photoaffinitive Labeling Reagent").

The present inventors discovered that photoreactive compounds newly developed during the aforementioned research into photoaffinity methods are particularly suited to substrate modification by polyamines in the production of DNA chips and protein chips, and that the aforementioned problems can be solved by making use thereof, thus to achieve the present invention.

That is, a first embodiment of the present invention is a novel compound represented by the following general formula (I):

(I)

wherein $R^1$ denotes a hydrogen atom, an optionally substituted alkyl group, an optionally substitute alkenyl group, an alkoxy group, a formyl group, a carboxyl group or a nitro group; and $R^2$ denotes a hydrogen atom, a halogen atom, or an alkyl group optionally substituted by a halogen atom.

Since these compounds have a photoreactive diazirine structure and a reactive epoxy group, they react with polyamines via the epoxy group, and can thus be used as raw materials for introducing photoreactive diazirine structures to polyamines.

A second embodiment of the present invention is a polyamine compound with an average molecular weight in the range of 2,000-150,000, wherein the amino groups and imino groups are at least partially substituted by a group represented by the following general formula (II):

(II)

wherein $R^1$ denotes a hydrogen atom, an optionally substituted alkyl group, an optionally substitute alkenyl group, an alkoxy group, a formyl group, a carboxyl group or a nitro group; $R^2$ denotes a hydrogen atom, a halogen atom, or an alkyl group optionally substituted by a halogen atom; and Z denotes an alkylene group having preferably 1-5, more preferably 1-3 carbon atoms, optionally substituted by a hydroxyl group.

More specifically, the group represented by general formula (II) preferably has a structure represented by one of the following general formulas (III) and (III'):

(III)

wherein $R^1$ and $R^2$ are defined as above;

(III')

wherein $R^1$ and $R^2$ are defined as above.

A third embodiment of the present invention is a method of producing a polyamine sheet by coating a substrate surface with a solution containing the above polyamine compound, then irradiating with UV rays to bind the polyamine compound to the substrate.

A fourth embodiment is a polyamine sheet produced by the above method.

The invention shall be described in further detail below.

For the purposes of the present invention, where not otherwise noted, "halogen atom" shall refer to fluorine atoms, chlorine atoms, bromine atoms and iodine atoms; "alkyl group" shall refer to straight or branched $C_{1-6}$ alkyl groups such as methyl, ethyl, propyl, isopropyl, butyl, isobutyl, sec-butyl, tert-butyl and pentyl groups; "alkenyl group" shall refer to straight or branched $C_{2-6}$ alkenyl groups such as vinyl, allyl and isopropenyl groups; and "alkoxy group" shall refer to straight or branched $C_{1-6}$ alkoxy groups such as methoxy, ethoxy, propoxy, isopropoxy or butoxy groups.

Additionally, for the purposes of the present invention, where not otherwise noted, "average molecular weight" shall refer to weight-average molecular weight.

Examples of substituent groups for the alkyl group, alkenyl group and alkoxy group in $R^1$ include halogen atoms, hydroxyl groups, alkoxy groups, carboxyl groups, nitro groups and amino groups.

Additionally, examples of the alkyl group optionally substituted by a halogen atom in $R^2$ include fluoromethyl, chloromethyl, fluoroethyl, difluoromethyl, trifluoromethyl and trichloromethyl groups, among which trifluoromethyl is preferable.

A specific example of a compound of general formula (1) is the following compound:

$R^{1a} = H$ (2)
$R^{1a} = OCH_3$ (2a)

In the present specification, "polyamine compound" shall refer to compounds having two or more amino groups or imino groups in the molecule. Examples include synthetic polymers such as polyalkyleneimines (e.g. polyethylenimine) and polyalkylamines (e.g. polyvinylamine and polyallyamine), and polyamino acids such as polyornithine and polylysine.

Specific examples of polyamine compounds with an average molecular weight in the range of 2,000-150,000, wherein the amino groups and imino groups are at least partially substituted by a group represented by the following general formula (II), include the following polyamine compounds (10)-(15).

Polyamine Compound (10)

(3)

(A)

(A)

The polyamine compound (10) includes repeating units represented by formula (3) and repeating units represented by formula (A), the molar ratios of which are preferably in the range of 1:50 to 1:2, more preferably 1:10 to 1:2.

The average molecular weight of the polyamine compound (10) is within the range of 2,000-100,000, preferably within the range of 5,000-80,000, and more preferably 10,000-50,000.

Polyamine Compound (11)

(4)

(B)

(B')

The polyamine compound (11) includes repeating units represented by formula (4) and repeating units represented by formula (B) and/or (B'), the molar ratios of which are preferably in the range of 1:50 to 1:2, more preferably 1:10 to 1:2. Additionally, the molar ratios of the repeating units represented by formula (B) and the repeating units represented by formula (B') may for example, be from 100:0 to 0:100.

The average molecular weight of the polyamine compound (11) is within the range of 2,500-150,000, preferably within the range of 2,500-120,000, and more preferably 3,000-100,000.

Polyamine Compound (12)

(6)

(C)

(C')

The polyamine compound (12) includes repeating units represented by formula (6) and repeating units represented by formula (C) and/or (C'), the molar ratios of which are preferably in the range of 1:50 to 1:2, more preferably 1:10 to 1:2.

Additionally, the molar ratios of the repeating units represented by formula (C) and the repeating units represented by formula (C') may, for example, be from 100:0 to 0:100.

The average molecular weight of the polyamine compound (12) is within the range of 2,000-150,000, preferably within the range of 2,500-120,000, and more preferably 3,000-100,000.

Polyamine Compound (13)

(7)

(A)

The polyamine compound (13) includes repeating units represented by formula (7) and repeating units represented by formula (A), the molar ratios of which are preferably in the range of 1:50 to 1:2.

The average molecular weight of the polyamine compound (13) is within the range of 2,000-100,000, preferably within the range of 5,000-80,000, and more preferably 10,000-50,000.

Polyamine Compound (14)

(8)

(B)

(B')

The polyamine compound (14) includes repeating units represented by formula (8) and repeating units represented by formula (B) and/or (B'), the molar ratios of which are preferably in the range of 1:50 to 1:2, more preferably 1:10 to 1:2.

Additionally, the molar ratios of the repeating units represented by formula (B) and the repeating units represented by formula (B') may, for example, be from 100:0 to 0:100.

The average molecular weight of the polyamine compound (14) is within the range of 2,000-150,000, preferably within the range of 2,500-120,000, and more preferably 3,000-10,000.

Polyamine Compound (15)

The polyamine compound (15) includes repeating units represented by formula (9) and repeating units represented by formula (C) and/or (C'), the molar ratios of which are preferably in the range of 1:50 to 1:2, more preferably 1:10 to 1:2.

Additionally, the molar ratios of the repeating units represented by formula (C) and the repeating units represented by formula (C') may, for example, be from 100:0 to 0:100.

The average molecular weight of the polyamine compound (15) is within the range of 2,000-150,000, preferably within the range of 2,500-120,000, and more preferably 3,000-10,000.

The compound of general formula (1) of the present invention may, for example, be produced by the following production method A.

[Production Method A]

(9)

(C)

(C')

In the formula, $R^1$ denotes a hydrogen atom, an optionally substituted alkyl group, an optionally substitute alkenyl group, an alkoxy group, a formyl group, a carboxyl group or a nitro group; and $R^2$ denotes a hydrogen atom, a halogen atom, or an alkyl group optionally substituted by a halogen atom.

The compound of general formula (2a) can be produced by epoxidation the compound of general formula (1a). This reaction may be achieved by a publicly known method of synthesis of an epoxide by an aldehyde (e.g. *Jikker Kagaku Kouza*, 4th ed., 20, 215-218 (1992), Maruzen). Specifically, for example, a methylene unit can be added by cycloaddition to the carbonyl of an aldehyde using dimethyisulfonium methylide or the like in a solvent of aqueous acetonitrile.

The compound of general formula (1a) can, for example, be prepared by the methods described in *Heterocycls*, 49, 465-468 (1998) and *J. Am. Chem. Soc.*, 115, 3458-3474 (1993), or methods similar thereto.

The polyamine compounds of the present invention may, for example, be produced by the following production methods B1-B3.

[Production Method B1]

In the formula, $R^1$ denotes a hydrogen atom, an optionally substituted alkyl group, an optionally substitute alkenyl group, an alkoxy group, a formyl group, a carboxyl group or a nitro group; and $R^2$ denotes a hydrogen atom, a halogen atom, or an alkyl group optionally substituted by a halogen atom.

Normally, epoxy compounds undergo ring-opening under mild conditions due to a nucleophilic substitution reaction of amines, to generate 2-aminoalcohol derivatives. This is specifically illustrated as Production Method B1.

A preferable example of a polyalkyleneimine used in the present invention is the polyethylenimine represented by the following formula.

The polyethylenimine used in the present invention preferably has an average molecular weight of about 10,000, so given $(C_6H_{15}N_3)_n \approx 129 \times n$, n must be about 78.

A preferred example of a polyalkyl amine used in the present invention is a poly(allylamine hydrochloride) represented by the following formula.

The poly(allylamine hydrochloride) used in the present invention preferably has an average molecular weight of about 15,000, so given $(C_3H_8ClN)_n \approx 94 \times n$, n must be about 156.

A preferred example of a polyamino acid used in the present invention is a poly-L-lysine hydrobromide represented by the following formula.

The poly-L-lysine hydrobromide used in the present invention preferably has an average molecular weight of about 5,000-15,000, so given $(C_6H_{13}BrN_2O)_n \approx 209 \times n$, n must be about 24-72.

The aforementioned polyamines and compound of general formula (2a) can be allowed to react overnight in a mixed solvent of dimethylformamide-water (1:1) shielded from light at about 50° C., to produce (3A), (4A) and (5A) which are components of polyamine compounds (10), (11) and (12). Additionally, this reaction should preferably be performed in the presence of a base when using an acidic polyamine salt such as poly(allylamine hydrochloride) or poly-L-lysine hydrobromide. After the reaction ends, the solvent can be discarded and the remainder further purified by gel filtration or the like to result in the desired polyamine compound.

The elution of the polyamine compound in gel filtration can be confirmed by measurement of the absorption of light at 254 nm and 360 nm.

While production method B1 according to the formula appears to have a substituent phenyl group added to all of the amino groups, in the actual polyamine compounds of the present invention, some of the amino groups in the polyamine exist as free amino groups (amino groups without substituent phenyl groups added).

Additionally, polyamine compounds (10), (11) and (12) are copolymers consisting of a plurality of repeating units of (3A), (4A) and (5A), and polyalkyleneimines, polyalkylamines and polyamino acids, wherein the repeating units in the respective polyamine compounds are arranged randomly.

[Production Method B2]

specific compound is 3-(4-(bromomethyl)-3-(trifluoromethyl)-3H-diazirine.

Normally, halogenated alkyl compounds and amines readily bind under mild conditions due to a nucleophilic substitution reaction in the presence of a base. This is specifically illustrated as Production Method B2.

Examples of the polyalkyleneimine, polyalkylamine and polyamino acid in Production Method B2 include, for example, polyethylenimine, polyallylamine and poly-L-lysine.

The aforementioned polyamines and compound of general formula (5A) wherein X is bromine can be allowed to react overnight in a mixed solvent of dimethylformamide-water (1:1) shielded from light at about 50° C., then after the reaction ends, the solvent can be discarded and the remainder further purified by gel filtration or the like to result in (6A), (7A) and (8A) which are components of the desired polyamine compounds (13), (14) and (15).

The elution of the polyamine compound in gel filtration can be confirmed by measurement of the absorption of light at 254 nm and 360 nm.

In the formula, $R^1$ denotes a hydrogen atom, an optionally substituted alkyl group, an optionally substitute alkenyl group, an alkoxy group, a formyl group, a carboxyl group or a nitro group; and $R^2$ denotes a hydrogen atom, a halogen atom, or an alkyl group optionally substituted by a halogen atom; and X denotes a halogen atom.

The compound of general formula (5A) can be produced by the method described in *J. Am. Chem. Soc.*, 106, 7540-7545 (1984), or methods similar thereto. An example of a While production method B2 according to the formula appears to have a substituent phenyl group added to all of the amino groups, in the actual polyamine compounds of the present invention, some of the amino groups in the polyamine exist as free amino groups (amino groups without substituent phenyl groups added).

Additionally, polyamine compounds (13), (14) and (15) are copolymers consisting of a plurality of repeating units of (6A), (7A) and (8A), and polyalkyleneimines, polyalkylamines and polyamino acids, wherein the repeating units in the respective polyamine compounds are arranged randomly.

[Production Method B3]

In the formula, $R^1$ denotes a hydrogen atom, an optionally substituted alkyl group, an optionally substitute alkenyl group, an alkoxy group, a formyl group, a carboxyl group or a nitro group; and $R^2$ denotes a hydrogen atom, a halogen atom, or an alkyl group optionally substituted by a halogen atom; and X denotes a halogen atom.

The compound of general formula (1a) can be produced by the method described in *Heterocycls*, 49, 465-468 (1998), or methods similar thereto. An example of a specific compound is 4-[3-trifluoromethyl-3H-diazirine-3-yl]benzoaldehyde.

Formyl compounds and amines can react under acidic conditions to form iminium compounds. These can be subjected to a reduction reaction using a reducing agent such as sodium cyanoborohydride ($NaCNBH_3$) to produce the desired polyamine compounds. This is specifically illustrated as Production Method B3.

Examples of the polyalkyleneimine, polyalkylamine and polyamino acid in Production Method B2 include, for example, polyethylenimine, polyallylamine and poly-L-lysine.

The aforementioned polyamines and compound (1) can be allowed to react for one day in a mixed solvent of acetic acid-water-methanol (7:1:8) shielded from light at about 50° C., then after adding $NaCNBH_3$, further allowing to react for one day shielded from light at about 50° C.

After the reaction ends, the solvent can be discarded and the remainder further purified by gel filtration or the like to result in (6A), (7A) and (8A) which are components of the desired polyamine compounds (13), (14) and (15).

The elution of the polyamine compound in gel filtration can be confirmed by measurement of the absorption of light at 254 nm and 360 nm.

While production method B3 according to the formula appears to have a substituent phenyl group added to all of the amino groups, in the actual polyamine compounds of the present invention, some of the amino groups in the polyamine exist as free amino groups (amino groups without substituent phenyl groups added).

Additionally, polyamine compounds (13), (14) and (15) are copolymers consisting of a plurality of repeating units of (6A), (7A) and (3A), and polyalkyleneimines, polyalkylamines and polyamino acids, wherein the repeating units in the respective polyamine compounds are arranged randomly.

[Polyamine Sheet Production Method]

The present invention also includes coating of a solution containing the polyamine compound (10), (11), (12), (13), (14) or (15) onto a substrate surface, then irradiating with UV rays to bind the polyamine compounds to the substrate surface.

The amine sheet can, for example, be prepared under the following scheme. While a substituent phenyl group appears to be added to all of the amino groups in the formula, in the actual polyamine compounds of the present invention, some of the amino groups in the polyamine exist as free amino groups (amino groups without substituent phenyl groups added).

photoreactive polyamine amine sheet

A coating solution containing a polyamine compound may be prepared in the following way.

For the solvent to be used in the coating solution, water is normally used, but depending on the physical properties such as solubility of the photoreactive polyamine, solvents other than water, such as various buffers and dimethylformamide, may be used, whether alone or in mixture.

While the blending ratio of polyamine compounds and solvent is not particularly limited as long as the amount is sufficient to dissolve the polyamine compounds, in the case of polyamine compound (12), 0.01-10 mg of polyamine compound (12) dissolved in 1 ml of solvent may be used. Other polyamine compounds may also be blended under roughly the same conditions.

The above coating solution is coated on the substrate surface. It is preferable for at least the surface of the substrate to be composed of a resin. As shown in the above scheme, the resin substrate has methyl groups on its surface, and these methyl groups react with the diazirine groups of the polyamine compounds when subjected to ultraviolet irradiation.

Diazirine, being a photoreactive group, creates carbenes, an active species with an extremely high reactivity, when irradiated by light, which easily create new bonds by insertion between chemical bonds in alkyl chains and the like. Therefore, immobilization to normal resin substrates is basically possible, but as shown in the abovementioned reaction scheme, the reactivity becomes high when a resin that has methyl groups on the surface is used. There are many examples of such resin substrates, such as polypropylene and methacrylate.

In order to induce a reaction in the polyamine compounds on the surface of the resin substrate, they are irradiated by ultraviolet rays. With regard to the ultraviolet irradiation, light in the vicinity of 350 nm, the light absorption band of diazirine, is necessary, and such light can, for example, be obtained from a 100 W blacklight lamp.

The specific procedure for preparing a polyamine sheet might involve spotting a polypropylene sheet with an appropriate amount of an aqueous solution (for example, 1.0 mg/ml) of polyamine compound, and drying. After irradiation for 30 minutes with a 100 W blacklight lamp, the result is washed sequentially with ion exchanged water, 1M hydrochloric acid, and ultrapure water.

In the present invention, a photoreactive polymer, obtained by modifying a polymer with diazirine which is photoreactive, is synthesized, placed on a solid phase and exposed to light, forming covalent bonds with the polymer at any location in the solid phase.

The reactive polyamines of the present invention can be baked onto polypropylene by a photoreaction, to prepare a new type of amine sheet.

Effects of the Invention (1) In the polyamine sheet of the present invention, the polyamines can be immobilized precisely at any location, and since they are immobilized by covalent bonds, contaminants due to non-specific adsorption or the like can be completely washed away and removed. Additionally, the reaction progresses efficiently with light in the neighborhood of 360 nm which is mostly unabsorbed by normal biological molecules such as DNA and proteins, and the reaction is moreover extremely fast, thus having little influence on the analysis system used.

(2) The polyamine sheet of the present invention does not require any special treatments on the resins of the substrate prior to spotting, thus enabling DNA ships to be prepared quickly and conveniently at a low cost.

(3) In the polyamine sheet of the present invention, the immobilized polyamines have a flexible three-dimensional structure, thus making the subsequent reaction system of the biological substance closer to a liquid phase environment, and also enabling the amount of substance immobilized per unit area to be increased.

(4) With the polyamine sheet of the present invention, when DNA are electrostatically immobilized on the substrate, the binding and removal of oligommers and DNA can be easily performed by adjusting the pH.

BEST MODE FOR CARRYING OUT THE INVENTION

Examples

Herebelow, working examples and test examples of the present invention shall be explained, but the present invention is not to be construed as being limited thereto.

In the following reaction formulas, the polyamine compounds are shown with substituent phenyl groups on all of the amino groups for the sake of convenience, but in the actual polyamine compounds of the present invention, some of the amino groups in the polyamine exist as amino groups without substituent phenyl groups added.

Example 1-1

Synthesis of 3-(4-oxiranylphenyl)-3-trifluoromethyl-3H-diazirine 0.95 g of trimethylsulfonium iodide and 0.52 g of potassium hydroxide were dissolved in 4 ml of acetonitrile, and agitated for 10 minutes at 60° C. in a nitrogen gas atmosphere. 1.00 g of 4-(3-trifluoromethyl-3H-diazirine-3-yl)benzaldehyde were added together with 5.3 ml of acetonitrile, then 0.02 g of water were added. This was agitated for one hour at 60° C. in a nitrogen gas atmosphere. After extracting with ethyl ether, the resulting substance was washed twice with water and once with saturated saline solution, then dried with anhydrous magnesium sulfate, and filtered. The solvent was removed under reduced pressure, and the resulting substance was purified by silica gel chromatography (hexane:chloroform=1:2, V/V) to obtain 0.56 g of 3-(4-oxiranylphenyl)-3-trifluoromethyl-3H-diazirine (52% yield).

$^1$H NMR (500 MHz, CDCl$_3$, 25° C.): δ7.31 (d, 2H, J=8.3 Hz), 7.18 (d, 2H, J=7.9 Hz), 3.81 (dd, 1H, J=2.6, 3.8 Hz), 3.17 (dd, 1H, J=5.6, 3.8 Hz), 2.75 (dd, 1H, J=2.6, 5.6 Hz).

Example 1-2

Synthesis of 3-(3-methoxy-4-oxiranylphenyl)-3-trifluoromethyl-3H-diazirine 488 mg of trimethylsulfonium iodide and 224 mg of potassium hydroxide were dissolved in 4 ml of acetonitrile, and agitated for 10 minutes at 60° C. in a nitrogen gas atmosphere. 488 mg of 3-methoxy-4-(3-trifluoromethyl-3H-diazirine-3-yl) benzaldehyde were added together with acetonitrile, then 9 μg of water were added. This was agitated for one hour at 60° C. in a nitrogen gas atmosphere. After extracting with ethyl ether, the resulting substance was washed twice with water and once with saturated saline solution, then dried with anhydrous magnesium sulfate, and filtered. The solvent was removed under reduced pressure, and the resulting substance was purified by silica gel chromatography (hexane:chloroform=3:2, V/V) to obtain 249 mg of 3-(3-methoxy-4-oxiranylphenyl)-3-trifluoromethyl-3H-diazirine (48% yield).

$^1$H NMR (500 MHz, CDCl$_3$, 25° C.): δ7.17 (d, 1H, J=8.1 Hz), 6.79 (d, 1H, J=8.1 Hz), 6.62 (2, 1H), 4.16 (dd, 1H, J=2.6, 3.8 Hz), 3.87 (s, 3H), 3.15 (dd, 1H, J=3.8, 6.0 Hz), 2.64 (dd, 1H, J=2.6, 6.0 Hz).

Example 2

Synthesis of photoreactive polyethylenimine (3)

(3)

20 mg of 3-(4-oxiranylphenyl)-3-trifluoromethyl-3H-diazirine, 11.2 mg of polyethylenimine (molecular weight 10,000, n in formula about 78), 2 ml of water and 2 ml of dimethylformamide were poured into an amber bottle, then agitated overnight in a 50° C. oil bath. The solvent was completely removed under reduced pressure, and 4 ml of water were added. The solution was subjected to gel filtration* (solvent: water) by a column 1 ml at a time, for purification. The light absorption of diazirine was monitored at 360 nm and 254 nm, then the photoreactive polyamine fraction was recovered and freeze-dried. The progress in the reaction was observed by thin-layer chromatography.

*Column: (gel portion) inner diameter 0.75 cm, height 18 cm, volume 31.8 cm$^3$

Gel: Sephadex G15

Fraction: batched into test tubes about 0.7 ml at a time

Figure 1:
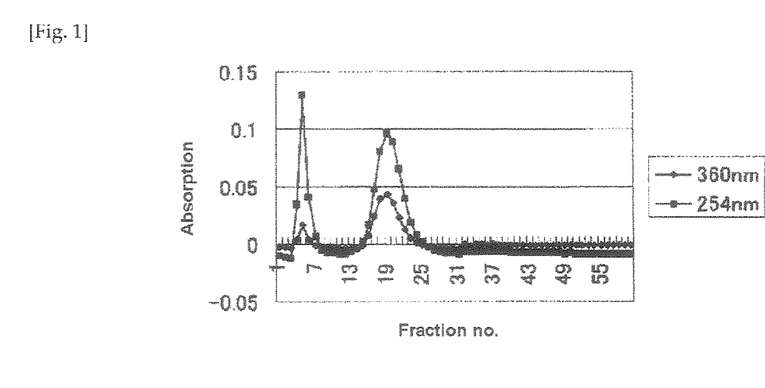
FIG. 1 Shows an elution pattern for gel filtration of Example 2.

The elution pattern is shown in FIG. 1.

Example 3

Synthesis of photoreactive polyallyamine (4)

20 mg of 3-(4-oxiranylphenyl)-3-trifluoromethyl-3H-diazirine, 8.2 mg of polyallylamine hydrochloride (molecular weight 15,000, n in formula about 156), 22.6 mg of diisopropyethylamine, 2 ml of water and 2 ml of dimethylformamide were poured into an amber bottle, then agitated overnight in a 50° C. oil bath. The solvent was completely removed under reduced pressure, and 4 ml of water were added. The solution was subjected to gel filtration* (solvent: water) by a column 1 ml at a time, for purification. The light absorption of diazirine was monitored at 360 nm and 254 nm, then the photoreactive polyamine fraction was recovered and freeze-dried. The progress in the reaction was observed by thin-layer chromatography.

*Column: (gel portion) inner diameter 0.75 cm, height 18 cm, volume 31.8 cm$^3$

Gel: Sephadex G15

Fraction: batched into test tubes about 0.7 ml at a time

Figure 2:
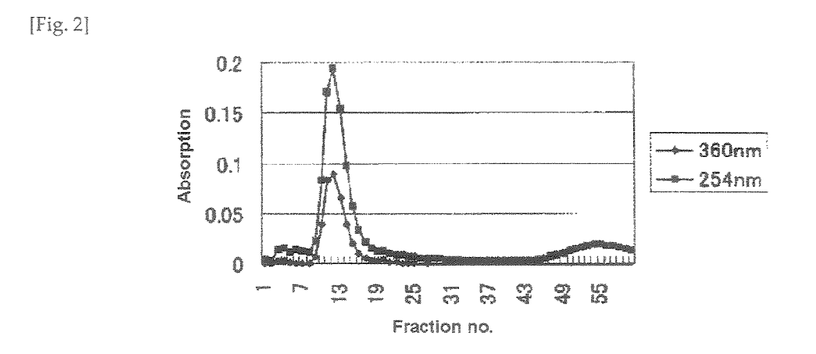
FIG. 2 Shows an elution pattern for gel filtration of Example 3.

The elution pattern is shown in FIG. 2.

Example 4

Synthesis of photoreactive poly-L-lysine (6)

(6)

40 mg of 3-(4-oxiranylphenyl)-3-trifluoromethyl-3H-diazirine, 36.6 mg of ply-L-lysine hydrobromide (molecular weight 5,000-15,000, n in formula about 24-72), 45.3 mg of diisopropyethylamine, 4 ml of water and 4 ml of dimethylformamide were poured into an amber bottle, then agitated overnight in a 50° C. oil bath. The solvent was completely removed under reduced pressure, and 8 ml of water were added. The solution was subjected to gel filtration* solvent: water) by a column 2 ml at a time, for purification. The light absorption of diazirine was monitored at 360 nm and 254 nm, then the photoreactive polyamine fraction was recovered and freeze-dried. The progress in the reaction was observed by thin-layer chromatography.

*Column: (gel portion) inner diameter 0.75 cm, height 36 cm, volume 63.6 cm³

Gel: Sephadex C15

Fraction: batched into test tubes about 1 ml at a time

Figure 3:
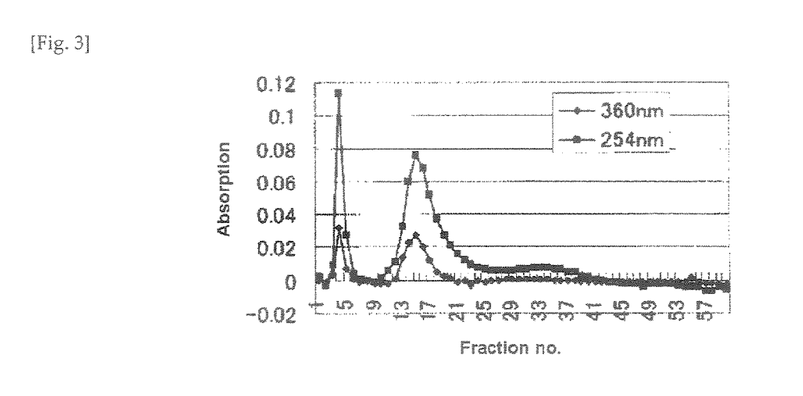
FIG. 3 Shows an elution pattern for gel filtration of Example 4.

The elution pattern is shown in FIG. 3.

TABLE 1

|  | C (%) | H (%) | N (%) |
|---|---|---|---|
| Element Content of Photoreactive Polyamine | | | |
| Theoretical value *1 | 43.95 | 4.61 | 12.81 |
| Measured result | 45.57 | 5.11 | 12.85 |
| Element Content of Polyamine *2 | | | |
| Theoretical value *3 | 33.32 | 6.43 | 12.95 |
| Measured result | 33.49 | 6.16 | 12.56 |

*1 When 100% diazirine-modified, for (L-lysine)$_{50}$ · (phenyldiazirine)$_{50}$ · 50 HBr
*2 Same conditions as synthesis, purification conditions for above photoreactive polyamine, but no diazirine compound (2) added.
*3 For (L-lysine)$_{50}$ · 50 HBR · 22 H$_2$O Light Absorption Absorption for 10× dilution of photoreactive polyamine 1.20 mg/water 1.0 ml: 0.0806

Value of $\epsilon$ for diazirine epoxide: 151

(Wavelength: 356 nm), (Solvent: water:methanol=4:1)

Given the above two values and the formula A=$\epsilon$ cl,

Modification of polyamines by diazirine: $4.44 \times 10^{-3}$ mol/1.00 mg

Example 5

Synthesis of photoreactive polyethylenimine (7)

20 mg of 3-(4-(bromomethyl)phenyl)-3-trifluoromethyl-3H-diazirine, 9.2 mg of polyethylenimine, 2 ml of water and 2 ml of dimethylformamide were poured into an amber bottle, then agitated overnight in a 50° C. oil bath. The solvent was completely removed under reduced pressure, and 4 ml of water were added. The solution was subjected to gel filtration* (solvent: water) by a column 1 ml at a time, for purification. The light absorption of diazirine was monitored at 360 nm and 254 nm, then the photoreactive polyamine fraction was recovered and freeze-dried. The progress in the reaction was observed by thin-layer chromatography.

*Column: (gel portion) inner diameter 0.75 cm, height 18 cm, volume 31.8 cm³

Gel: Sephadex G15

Fraction batched into test tubes about 0.7 ml at a time

Figure 4:
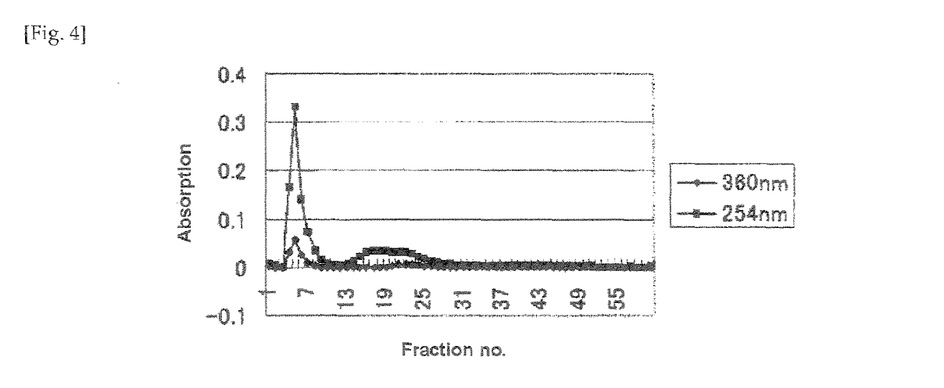
FIG. 4 Shows an elution pattern for gel filtration of Example 5.

The elution pattern is shown in FIG. 4.

Example 6

Synthesis of photoreactive polyallylamine (8)

20 mg of 3-(4-(bromomethyl)phenyl)-3-trifluoromethyl-3H-diazirine, 6.6 mg of polyallylamine hydrochloride, 2 ml of water and 2 ml of dimethylformamide were poured into an amber bottle, then agitated overnight in a 50° C. oil bath. The solvent was completely removed under reduced pressure, and 4 ml of water were added. The solution was subjected to gel filtration* (solvent: water) by a column 1 ml at a time, for purification. The light absorption of diazirine was monitored at 360 nm and 254 nm, then the photoreactive polyamine fraction was recovered and freeze-dried. The progress in the reaction was observed by thin-layer chromatography.

*Column: (gel portion) inner diameter 0.75 cm, height 18 cm, volume 31.8 cm³

Gel: Sephadex G15

Fraction: batched into test tubes about 0.7 ml at a time

Figure 5:
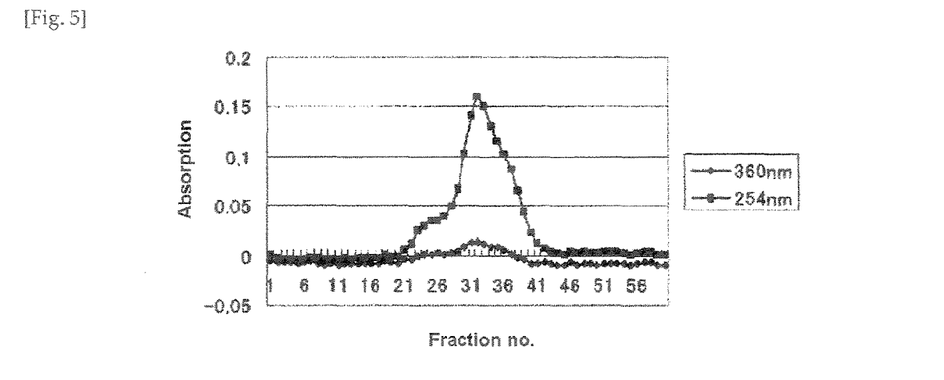
FIG. 5 Shows an elution pattern for gel filtration of Example 6.

The elution pattern is shown in FIG. 5.

Example 7

Synthesis of photoreactive poly-L-lysine (9)

(9)

20 mg of 3-(4-(bromomethyl)phenyl)-3-trifluoromethyl-3H-diazirine, 15.1 mg of poly-L-lysine hydrobromide, 2 ml of water and 2 ml of dimethylformamide were poured into an amber bottle, then agitated overnight in a 50° C. oil bath. The solvent was completely removed under reduced pressure, and 4 ml of water were added. The solution was subjected to gel filtration* (solvent: water) by a column 1 ml at a time, for purification. The light absorption of diazirine was monitored at 360 nm and 254 nm, then the photoreactive polyamine fraction was recovered and freeze-dried. The progress in the reaction was observed by thin-layer chromatography.

*Column: (gel portion) inner diameter 0.75 cm, height 18 cm, volume 31.8 cm³

Gel: Sephadex C15

Fraction: batched into test tubes about 0.7 ml at a time

Figure 6:
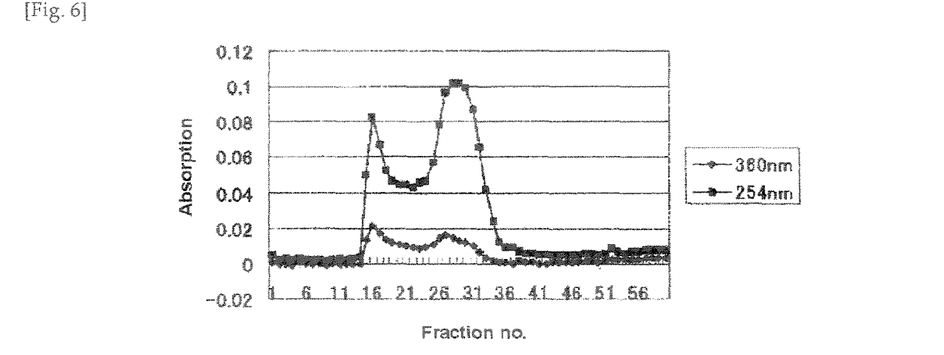
FIG. 6 Shows an elution pattern for gel filtration of Example 7.

The elution pattern is shown in FIG. 6.

Example 8

Synthesis of photoreactive polyethylenimine (7)

17 mg of polyethylenimine, 700 μl of acetic acid and 100 μl of water were poured into an amber bottle, and the bottle was shaken to dissolve the polyethylenimine. Next, 28 mg of 4-[3-trifluoromethyl-3H-diazirine-3-yl]benzaldehyde and 800 μl of methanol were added, the result agitated for 24 hours in a 50° C. oil bath, then the solvent was removed under reduced pressure. About one scoop of a spatula of sodium cyanoborohydride and 1.6 ml of methanol were added, then the result was agitated for 24 hours in a 50° C. oil bath. The solvent was completely removed under reduced pressure, and 1 ml of water were added. The solution was subjected to gel filtration* (solvent: water) by a column for purification. The light absorption of diazirine was monitored at 360 nm and 254 nm, then the photoreactive polyamine fraction was recovered and freeze-dried. The progress in the reaction was observed by thin-layer chromatography.

*Column: (gel portion) inner diameter 0.75 cm, height 18 cm, volume 31.8 cm³

Cel: Sephadex C15

Fraction: batched into test tubes about 1 ml at a time

Figure 7:
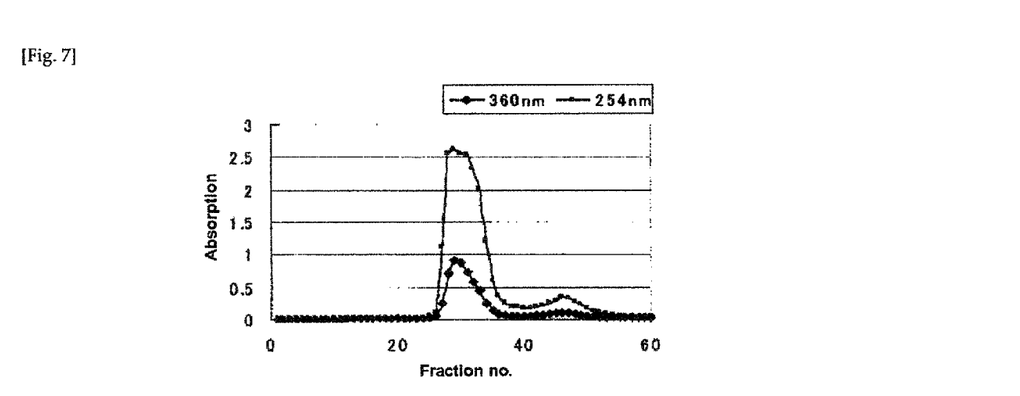
FIG. 7 Shows an elution pattern for gel filtration of Example 8.

The elution pattern is shown in FIG. 7.

Example 9

Preparation of Amine Sheet

PP sheet amine sheet

10 µl of a solution having compound (3) dissolved in water were placed on a polypropylene sheet (thickness 0.2 cm, width 3.5 cm, length 3.0 cm), then dried in a draft. Next, a UV lamp was used to irradiate the sheet with UV rays from above and below for 30 minutes at intervals of 4 cm. Then, the sheet was vigorously washed with ion-exchanged water, rinsed with 1 M hydrochloric acid, and rinsed with ultrapure water (Milli-Q System by Millipore) to obtain the polyamine sheet of the present invention. The immobilization of polyamines to the sheet was confirmed by a ninhydrin reaction.

Test Example 1

Figure 8:
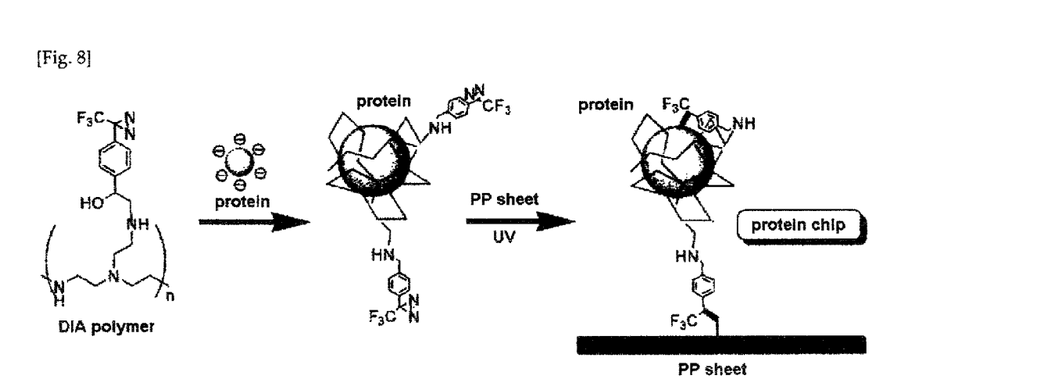
FIG. 8 Conceptual diagram showing immobilization of proteins to a polyamine sheet.

Immobilization of proteins to polyamine sheet (conceptual diagram shown in FIG. 8.)

A mixed solution of 5 µl of a 1% (W/V) aqueous solution of DIA-polyethylenimine and 5 µl of a 1% (W/V) aqueous solution of horseradish peroxidase was spotted onto a polypropylene sheet and dried for 20 minutes under reduced pressured. Next, after irradiation with UV rays (360 nm, 15 W×2 for 60 minutes), the result was ultrasonically washed for 1 minute in a buffer solution.

The activity of HRP immobilized on the sheet was confirmed by luminol luminescence.

INDUSTRIAL APPLICABILITY

A photoreactive polymer having a diazirine group, commonly used in the photoaffinity process which is an effective method for analyzing the structure and function of bioactive substances, introduced to polyamines is produced. By spotting onto a solid phase such as polypropylene and irradiating with light, the polyamines can be immobilized by covalent bonds. This lithography enables functional group structures to be provided at arbitrary locations even of the surfaces of resins which are low in chemical reactivity.

The invention claimed is:

1. A compound represented by the following general formula (I):

wherein $R^1$ denotes a hydrogen atom, an optionally substituted alkyl group, an optionally substitute alkenyl group, an alkoxy group, a formyl group, a carboxyl group or a nitro group; and $R^2$ denotes a hydrogen atom, a halogen atom, or an alkyl group optionally substituted by a halogen atom.

2. A compound in accordance with claim 1, represented by the following general formula:

wherein $R^{1a}$ denotes a hydrogen atom or a methoxy group.

* * * * *

UNITED STATES PATENT AND TRADEMARK OFFICE
CERTIFICATE OF CORRECTION

PATENT NO. : 8,043,666 B2
APPLICATION NO. : 11/573824
DATED : October 25, 2011
INVENTOR(S) : Yasumaru Hatanaka et al.

It is certified that error appears in the above-identified patent and that said Letters Patent is hereby corrected as shown below:

Column 5, lines 60 – 65 "  " should be deleted as it duplicates the identical formula in Column 5, lines 55-59.

Column 6, lines 34 – 48 "  " should be read

Signed and Sealed this
Twenty-third Day of October, 2012

David J. Kappos
*Director of the United States Patent and Trademark Office*